(12) United States Patent
Basit et al.

(10) Patent No.: US 9,023,368 B2
(45) Date of Patent: May 5, 2015

(54) COLONIC DRUG DELIVERY FORMULATION

(75) Inventors: Abdul Waseh Basit, Middlesex (GB); Valentine Chidi Ibekwe, London (GB)

(73) Assignee: University College London, London (GB)

( * ) Notice: Subject to any disclaimer, the term of this patent is extended or adjusted under 35 U.S.C. 154(b) by 931 days.

(21) Appl. No.: 11/735,248

(22) Filed: Apr. 13, 2007

(65) Prior Publication Data

US 2007/0243253 A1 Oct. 18, 2007

(30) Foreign Application Priority Data

Apr. 13, 2006 (GB) .................................. 0607534.5

(51) Int. Cl.
*A61K 9/00* (2006.01)
*A61K 9/28* (2006.01)
*A61K 31/573* (2006.01)
*A61K 31/60* (2006.01)

(52) U.S. Cl.
CPC ................ *A61K 9/286* (2013.01); *A61K 9/284* (2013.01); *A61K 31/573* (2013.01); *A61K 31/60* (2013.01)

(58) Field of Classification Search
None
See application file for complete search history.

(56) References Cited

U.S. PATENT DOCUMENTS

| 5,294,448 | A | * | 3/1994 | Ring et al. ..................... 424/497 |
| 5,422,121 | A | * | 6/1995 | Lehmann et al. ............. 424/464 |
| 6,251,430 | B1 | | 6/2001 | Zhang et al. |
| 2007/0276047 | A1 | * | 11/2007 | Oberegger et al. ........... 514/649 |

FOREIGN PATENT DOCUMENTS

| EP | 0 343 993 A1 | 11/1989 |
| EP | 1 203 590 A1 | 5/2002 |
| GB | 2 367 002 A | 3/2002 |
| WO | WO 91/07949 | 6/1991 |
| WO | WO 99/21536 | 5/1999 |
| WO | WO 99/25325 | 5/1999 |
| WO | WO 99/52512 * | 9/1999 |
| WO | WO 01/76562 A1 | 10/2001 |
| WO | WO 03/068196 A1 | 8/2003 |
| WO | WO 2004/052339 A1 | 6/2004 |
| WO | WO 2007/013794 A1 | 2/2007 |

OTHER PUBLICATIONS

A. W. Basit, et al., "The Use of Formulation Technology to Assess Regional Gastrointestinal Drug Absorption in Humans", European Journal of Pharmaceutical Sciences, 21, 2004, pp. 179-189.
S. Milojevic, et al., "Amylose as a Coating for Drug Delivery to the Colon: Preparation and In Vitro Evaluation Using 5-Aminosalicylic Acid Pellets", Journal of Controlled Release, 38, 1996, pp. 75-84.
A. Akhgari, et al., "Permeability and Swelling Studies on Free Films Containing Insulin in Combination With Different Polymethacrylates Aimed for Colonic Drug Delivery", European Journal of Pharmaceutical Sciences, 28, 2006, pp. 307-314.
K. Krogars, et al., "Tablet Film-Coating With Amylose-Rich Maize Starch", European Journal of Pharmaceutical Sciences, 17, 2002, pp. 23-30.

* cited by examiner

*Primary Examiner* — Snigdha Maewall
(74) *Attorney, Agent, or Firm* — Oblon, McClelland, Maier & Neustadt, L.L.P.

(57) ABSTRACT

A delayed release coating comprising a mixture of a first material selected from starch; amylose; amylopectin; chitosan; chondroitin sulfate; cyclodextrin; dextran; pullulan; carrageenan; scleroglucan; chitin; curdulan and levan, and a second material which has a pH threshold at about pH 5 or above, is used to target release of a drug from a core to the intestine, particularly the colon.

28 Claims, 9 Drawing Sheets

COLONIC DRUG DELIVERY FORMULATION

The present invention relates to a delayed release formulation with a core comprising a drug and a delayed release coating. In particular, it relates to a delayed release formulation for a drug for delivering to the colon.

The targeting of drugs to the colon can be utilised as a means of achieving local therapy or systemic treatment. The colon is susceptible to a number of disease states, including inflammatory bowel disease, irritable bowel syndrome, constipation, diarrhoea, infection and carcinoma. In such conditions, drug targeting to the colon would maximise the therapeutic effectiveness of the treatment. The colon can also be utilised as a portal for the entry of drugs into the systemic circulation. Various formulations have been developed for colonic drug delivery, including pro-drugs as well as formulated dosage forms, with the latter being more popular since the concept once proved can be applied to other drugs.

The higher bacterial population in the colon has also been exploited in developing colonic drug delivery dosage forms through the use, as carrier materials, of naturally occurring complex polysaccharides that constitute substrates for the numerous enzymes of the resident colonic bacteria. These materials are able to pass through the upper gastrointestinal regions intact but are digested upon entry into the colon. Those studied so far include amorphous amylose, pectin, chitosan and galactomannan.

Amorphous amylose is resistant to digestion by the enzymes the upper gastrointestinal tract. It is, however, fermented in the colon by α-amylase enzymes produced by over half of the 400 bacteria species resident in the colon.

One major attraction of using polysaccharides in this bacterial enzyme approach to colonic drug delivery is that materials used are of food grade and so would be safe for use in humans. They are usually applied as coatings or incorporated in the core material as a matrix carrier, and their digestion on entry into the colon by the colonic bacterial enzymes leads to the release of the drug load. An example of such a formulation, which employs an amylose coating, is disclosed in EP-A-0343993 (BTG International Limited).

A major limitation with these naturally occurring materials, however, is that they swell excessively in aqueous media leading to leaching of the drug load in the upper gastrointestinal regions. To circumvent this problem, they have been utilised in a mixture with impermeable materials (e.g. amorphous amylose mixed with the water-insoluble polymer ethylcellulose). However, the problem with such modifications/mixtures is in finding the right balance between hydrophobicity and hydrophilicity that would prevent inopportune drug release in the upper gastrointestinal regions, but which would also at the same time permit enzyme access to the polysaccharide substrate and ensure drug release at an adequate rate in the colon.

An attempt to solve the problem of the excessive swelling of amylose is disclosed in EP-A-0502032 (British Technology Group Ltd). This employs an outer coating comprising a film forming cellulose or acrylate polymer material and amorphous amylose for a tablet comprising an active compound. One embodiment has the active compound coated first with an inner coating of amylose and then a separate outer coating of the cellulose or acrylate polymer material. Another embodiment has an outer coating which is an admixture of amylose and a cellulose or acrylate polymer. The reference makes clear that the degradation of the cellulose materials in vivo is, in general, not pH dependent and it is preferred that this is also true for the acrylate materials. Every example disclosed in the reference is of a pH independent cellulosic or acrylate polymer.

An article in Journal of Controlled Release (Milojevic et al; 38; (1996); 75-84) reports the results of investigations concerning the incorporation of a range of insoluble polymers into an amylose coating in order to control amylose swelling. A range of cellulose and acrylate based co-polymers are assessed, and a commercially available ethyl cellulose (Ethocel®) is found to control the swelling most effectively. Another single layer coating that is investigated is a mixture of amylose and two pH independent acrylic polymers, namely Eudragit® RS and RL, but this coating is found not to give such effective results. A pH dependent soluble coating of Eudragit® L100 is employed but only in a multi-layer system comprising bioactive coated with an inner coating of amylose and then an outer coating of Eudragit® L100.

A further amylose-based coating composition is disclosed in WO-A-99/21536 (ETC International Limited). The coating composition comprises a mixture of amylose and a water insoluble film-forming polymer which is formed from a water-insoluble cellulosic or acrylate polymer material. As with EP-A-0502032, it is made clear that degradation of the cellulose materials in vivo is, in general, not pH dependent and it is preferred that this is also true for the acrylate materials. It would appear that the PCT specification contains a typographical error, because it goes on to say that a preferred form of acrylate material is "Eudragit L whose degradation is independent of pH". It is believed that this should refer to "Eudragit® RL" whose degradation is indeed independent of pH. It cannot be intended to refer to Eudragit® L, as the degradation of this polymer is pH dependent.

WO-A-99/25325 (BTG International Limited) also discloses a delayed release coating comprising amylose and (preferably) ethyl cellulose or alternatively an acrylate polymer the degradation of which is independent of pH. The coating composition also includes a plasticiser and the method finds particular application in the preparation of dosage forms comprising active materials that are unstable at temperatures in excess of 60° C., as the composition is formed at lower temperatures than this. It should be noted that this reference also includes the typographical error relating to Eudragit® L described above.

The Inventors note that the formulations disclosed in the BTG references discussed above use in the coatings amylose rather than starch and that release from the formulations is sustained along a portion of the gut.

WO-A-03/068196 (Alizyme Theraputics Ltd) discloses a specific delayed release coating for the bioactive prednisolone sodium metasulphobenzoate comprising glassy amylose, ethyl cellulose and dibutyl sebacate.

The use of polysaccharides other than amorphous amylose in a delayed release coating is disclosed in GB-A-2367002 (British Sugar PLC). Examples include guar gum, karaya gum, gum tragacanth and xanthan gum. Microparticles of these polysaccharides are dispersed in a water-insoluble film-forming polymer matrix formed for example from a cellulose derivative, an acrylic polymer or a lignin.

WO-A-01/76562 (Tampereen Patenttitoimisto Oy) discloses peroral pharmaceutical formulation containing a drug and a chitosan (a polysaccharide obtained from chitin) for controlling its release. The drug and the chitosan are mixed into a homogeneous mechanical powder mixture which granulated and then optionally tabletised. The granulation may be performed with an enteric polymer (such as a copolymer of methacrylic acid) or the granules may be provided with a porous enteric coating.

WO-A-2004/052339 (Salvona LLC) discloses a pH dependent drug release system which is a free-flowing powder of solid hydrophobic nano-spheres comprising a drug encapsulated in a pH-sensitive micro-sphere. The nano-spheres are formed from the drug in combination with a wax material, and the pH-sensitive micro-sphere formed from a pH-sensitive polymer (such as a Eudragit® polymer) in combination with a water-sensitive material such as a polysaccharide. The present applicant believes however that the very small particle sizes involved in this reference would not in practice delay the release of the bioactive core, beyond the stomach or duodenum.

An article in the European Journal of Pharmaceutical Sciences (Akhgari et al; 28; March 2006; 307-314) reports the results of investigations into the use of certain polymethacrylate polymers to, inter alia, control the swelling of inulin. The polymethacrylate polymers tested were Eudragit® RS; Eudragit® RL; 1:1 mixtures of Eudragit® RS and Eudragit® RL; Eudragit® FS; and 1:1 mixtures of Eudragit® RS and Eudragit® S. Results indicated that polymer compositions comprising sustained release polymethacrylates (Eudragit® RS and Eudragit® RL; pH insensitive polymers) with inulin displayed swelling profiles indicating a suitability for use as coatings for colonic release. However, other results indicated that polymer compositions comprising inulin with either Eudragit® FS or 1:1 mixtures of Eudragit® RS and Eudragit® S (pH dependent polymers) would not be suitable for such use due to undesirable swelling profiles.

U.S. Pat. No. 5,422,121 (Röhm GmbH) discloses an oral dosage form containing at least one active ingredient enclosed within a shell material which comprises a polysaccharide that decomposes in the colon. The shell material contains a film-forming polymer in admixture with the polysaccharide. The ratio by weight of polysaccharide to film forming polymer is from 1:2 to 5:1, preferably from 1:1 to 4:1. Examples of suitable polysaccharides include those polysaccharides that are decomposable by glycosidic enzymes. Polysaccharides containing considerable amounts, preferably about 20 wt % to 100 wt %, of galactose and mannose units are particularly suitable with locust bean gum and guar gum being preferred. Preferred film-forming polymers include acrylate polymers that are pH independent (insoluble throughout the GI tract) and pH dependent (insoluble in stomach juice but soluble in intestinal juice at pH 5.5 or above). The reference exemplifies the use of a mixture of guar gum with either Eudragit RL 30 D (in a ratio of 41), Eudragit® L 30 D (in a ratio of 3:1) or Eudragit® S 100 (in a ratio of 2.5:1) as a tablet coating.

An article in the European Journal of Pharmaceutical Sciences (Krogars et al; 17; (2002); 23-30) discloses the use of Hylon™ VII (an amylose-rich (~70 wt %) maize starch; National Starch, Germany) as a film coating for tablets containing a drug (theophylline). Dissolution of the tablets in acidic medium was rapid with more than 75% of the drug being dissolved within 15 minutes. The coating did not contain a second film forming polymer.

In accordance with a first aspect of the present invention, there is provided a delayed release drug formulation comprising a particle with a core and a coating for the core, the core comprising a drug and the coating comprising a mixture of a first material which is susceptible to attack by colonic bacteria and a second material which has a solubility threshold at about pH 5 or above, wherein the first material comprises a polysaccharide selected from the group consisting of starch; amylose; amylopectin; chitosan; chondroitin sulfate; cyclodextrin; dextran; pullulan; carrageenan; scleroglucan; chitin; curdulan and levan.

The first material comprises a polysaccharide, preferably containing a plurality of glucose units. Preferably the polysaccharide is starch, amylose or amylopectin, most preferably starch.

It has surprisingly been discovered that the disadvantageous swelling of materials susceptible to attack by colonic bacteria, e.g. amylose, can be controlled by a pH dependent material which is soluble at pH 5 or above, in addition, the Inventors have discovered that, unexpectedly, coatings containing large proportions of amylopectin would also work to provide colonic release of a drug from an oral dosage formulation.

A further technical advantage of the present invention (compared, for example, to the formulation disclosed in WO-A-01/76562) is that substantially no drug is released for an extended period (that is, whilst the coating is being dissolved), following which the drug is released relatively quickly. This is in contrast to homogeneous tablets from which the drug release profile is gradual from the outset rather than delayed then pulsatile.

The person skilled in the art is capable of determining whether a material is susceptible to attack by colonic bacteria using techniques comprising part of the common general knowledge. For example, a pre-determined amount of a given material could be exposed to an assay containing an enzyme from a bacterium found in the colon and the change in weight of the material over time may be measured.

The polysaccharide preferably starch. Starches are usually extracted from natural sources such as cereals; pulses; and tubers. Suitable starches for use in the present invention are typically food grade starches and include rice starch; wheat starch; corn (or maize) starch; pea starch; potato starch; sweet potato starch; tapioca starch; sorghum starch; sago starch; and arrow root starch. The use of maize starch is exemplified below.

Starch is actually a mixture of two different polysaccharides, namely amylose and amylopectin. Different starches may have different proportions of these two polysaccharides. Most natural (unmodified) maize starches have from about 20 wt % to about 30 wt % amylose with the remainder being at least substantially made up of amylopectin. Starches suitable for use in the present invention typically have at least 0.1 wt %, e.g. at least 10% or 16%, preferably at least 35 wt %, amylose. "High amylose" starches, are starches having at least 50 wt % amylose. Particularly suitable starches have from about 65 wt % to about 75 wt %, e.g. about 70 wt % amylose.

Starches suitable for use in the present invention may have up to 100% amylopectin, more typically from about 0.1 wt % to about 99.9 wt % amylopectin. "Low amylose" starches, i.e. starches having no more than 50 wt % amylose and at least 50 wt % amylopectin, e.g. up to 75 wt % amylopectin and even as much as up to 99 wt % amylopectin, are suitable. The starch may be, for instance, unmodified waxy corn starch. This typically comprises about 100% amylopectin, "Low amylose" starch was not expected to be suitable, since low amylose starch is typically degraded by pancreatic enzymes in the small intestine. Preferred starches have no more than 50 wt % amylopectin. Particularly suitable starches have from about 25 wt % to about 35 wt % amylopectin, e.g. about 30 wt % amylopectin.

The person skilled in the art is capable of determining the relative proportions of amylose and amylopectin in any given starch. For example, near-infrared ("NIR") spectroscopy could be used to determine the amylose and amylopectin content of a starch using calibration curves obtained by NIR using laboratory-produced mixtures of known amounts of these two components. Further, starch could be hydrolysed to glucose using amyloglucosidase. A series of phosphorylation and oxidation reactions catalysed by enzymes result in the formation of reduced nicotinamide adenine dinucleotide phosphate ("NADPH"). The quantity of NADPH formed is stochiometric with the original glucose content. Suitable test kits for this procedure are available (e.g., R-Biopharm GmbH, Germany). Another method that could be used involves subjecting the coating to digestion by bacterial enzymes, e.g. α-amylase, to produce short chain fatty acids ("SCFA") which can be quantified by gas-liquid chromatography using a capillary column.

Preferred starches have amylose in its glassy form although amylose in its amorphous form may also be used in conjunction with the present invention.

Preferred starches are "off-the-shelf" starches, i.e. starches which require no processing prior to use in the context of the present invention. Examples of particularly suitable "high amylose" starches include Hylon™ VII (National Starch, Germany) or Eurylon™ 7 (Roquette, Lestrem, France) or Amylogel 03003 (Cargill, Minneapolis, USA) all of which are examples of a maize starch having about 70 wt % amylose.

The present invention involves the use of a second material which dissolves in a pH dependent manner. The second material has a "pH threshold" which is the pH below which it is insoluble and at or above which it is soluble. The pH of the surrounding medium triggers dissolution of the second material. Thus, none (or essentially none) of the second material dissolves below the pH threshold. Once the pH of the surrounding medium reaches (or exceeds) the pH threshold, the second material becomes soluble. By "insoluble" we mean that 1 g of the second material requires more than 10,000 ml of solvent (surrounding medium) to dissolve at a given pH. By "soluble", we mean that 1 g of the second material requires less than 10,000 ml, preferably less than 5,000 ml, more preferably less than 1000 ml, even more preferably less than 100 ml or 10 ml of solvent to dissolve at a given pH. Surrounding medium preferably means the medium in the gastro intestinal tract, such as the gastric juice or intestinal juice. Alternatively, the surrounding medium may be in the vitro equivalent of the medium in the gastrointestinal tract.

The normal pH of gastric juice is usually in the range of to 3. The second material is insoluble below pH 5 and soluble at about pH 5 or above and soluble at about pH 5 or above and, thus, is usually insoluble in gastric juice. Such a material may be referred to as an "enteric" material.

The second material is soluble at pH 5 or above, e.g. in intestinal juice. The pH of intestinal juice gradually increases from about 6 in the duodenum to about 7 to 8 in the colon. The second material is preferably insoluble below pH 6.5 (and soluble at about pH 6.5 or above) and, more preferably, is insoluble below pH 7 (and soluble at about pH 7 or above).

The pH threshold at which a material becomes soluble may be determined by a simple titration technique which would be part of the common general knowledge to the person skilled in the art.

The second material is typically a film-forming polymeric material such as an acrylate polymer, a cellulose polymer or a polyvinyl-based polymer. Examples of suitable cellulose polymers include cellulose acetate phthalate ("CAP"); cellulose acetate trimellitate ("CAT"); and hydropropylmethylcellulose acetate succinate. Examples of suitable polyvinyl-based polymers include polyvinyl acetate phthalate ("PVAP").

The second material is preferably a co-polymer of a (meth) acrylic acid and a (meth)acrylic acid $C_{1-4}$ alkyl ester, for instance, a copolymer of methacrylic acid and methacrylic acid methyl ester. Such a polymer is known as a poly(methacrylic acid/methyl methacrylate) co-polymer. Suitable examples of such co-polymers are usually anionic and not sustained release polymethacrylates. The ratio of carboxylic acid groups to methyl ester groups (the "acid:ester ratio") in these co-polymers determines the pH at which the co-polymer is soluble. The acid:ester ratio may be from about 2:1 to about 1:3, e.g. about 1:1 or, preferably, about 1:2. The molecular weight ("MW") of preferred anionic co-polymers is usually from about 120,000 to 150,000, preferably about 135,000.

Preferred anionic poly(methacrylic acid/methyl methacrylate) co-polymers include Eudragit® L (acid:ester ratio about 1:1; MW about 135,000; pH threshold of about 6.0); Eudragit® S (acid:ester ratio about 1:2; MW about 135,000; pH threshold of about 7); and Eudragit® FS (a poly(methyl acrylate/methyl methacrylate/methacrylic acid; acid:ester ratio of about 1:10; MW about 220,000; pH threshold of about 7.)

The second material may be a copolymer of methacrylic acid and ethyl acrylate. Eudragit® L100-55 poly(methacrylic acid/ethyl acrylate); acid:ester ratio of about 1:1; MW about 250,000; pH threshold of about 5.5 is suitable. The Eudragit® co-polymers are manufactured and/or distributed by Degussa AG, Darmstadt, Germany.

Mixtures of film forming polymer materials may be used appropriate. An example of a suitable mixture would include a mixture, e.g. a 1:1 mixture, of Eudragit® L and Eudragit® S. However, the use of a particular film forming polymer material, e.g. a poly(methacrylic acid/methyl methacrylate) co-polymer, alone is preferred.

The use of Eudragit® S alone as the second material is particularly preferred.

In a preferred embodiment, it has been found that mixture of two suitable polymers at an appropriate ratio, applied as a film coating on to a core, at least minimises, and can substantially eliminate, drug release in the stomach and small intestine. Subsequent drug release in the colon is believed to occur by the combined active physiological triggers: i.e. by dissolution of the second material, particularly Eudragit® S, and digestion of the first material, e.g. starch or amylose.

The proportion of the first material to the second material is typically less than 99:1 and may in some circumstances be up to 50:50. The proportion is usually up to 35:65 and is preferably from 15:85 to 35:65, e.g. 15:85 to 30:70. The Inventor has discovered that a ratio of first material to second material from about 25:75 to about 35:65, e.g. about 30:70, is particularly suitable for targeting release of the drug to the colon, particularly if the first material is starch and the second material is Eudragit® S. The mixture of first and second materials is preferably substantially homogenous.

Optionally, conventional excipients such as plasticisers for film formation (for example, triethyl citrate) and anti-tack agents (such as glyceryl monostearate) may be included in amounts up to 30% by weight of the final composition of the polymer coating preparation.

The thickness of the coating of the particle is typically from about 10 μm to about 150 μm. The thickness of a specific coating will, however, depend on the composition of the coating. For example, coating thickness is directly proportional to the amount of polysaccharide in the coating. Thus, in embodiments where the coating comprises high amylose starch and Eudragit™ S at a ratio of about 30:70, the coating thickness may be from about 70 μm to about 130 μm, and preferably from about 90 µm to about 110 µm. The thickness (in µm) for a given coating composition is independent of core size.

The thickness of the coating may also be measured by the "theoretical weight gain" ("TWG") of the coated formulation. The TWG for the present formulation will depend on a number of factors including the composition of the coating and the size of the core to be coated. For example, in embodiments where the core is a small tablet (e.g. having a diameter of about 8 mm) and the coating comprises high amylose starch and Eudragit™ S (e.g. in a ratio of about 30:70), the TWG is typically from about 4% to about 12%, e.g. from about 5% to about 10%, preferably from about 8% to about 9%. In embodiments where the core is a pellet (e.g. having a diameter of about 1 mm) having the same coating, the TWG may be from about 15% to about 35%, e.g. from about 20% to about 30%, preferably about 25%.

By saying that the coating comprises a mixture of the first and second materials, it is intended to exclude the known multi-layer dosage form (disclosed for example in Milojevic et al. described above) in which an active core is coated first with an inner coating of amylose and then with an outer coating of Eudragit® L100. In the context of the present invention, such a multi-layer dosage form does not comprise a mixture of starch and Eudragit® L100. The coating is preferably a single layer of a mixture of the first and second materials, preferably a homogenous mixture.

The formulation of the present invention may however have an additional layer either between the active core and the layer comprising the delayed release composition of the present invention and/or an outer layer coating the delayed release composition layer of the present invention. For example, if the delayed release composition layer comprises a mixture of Eudragit® L and starch, the addition of an outer layer of a pH dependent release coating material having a pH threshold of about 7, e.g. Eudragit® S, may be preferable. In preferred embodiments, the delayed release coating of the present invention is applied directly to the active core, i.e. there is no additional layer between this coating and the active core. The delayed release coating of the present invention is preferably the outer coating of the formulation. Advantageously, it has been found that no additional outer layer is required to ensure that the composition is a delayed release composition.

The composition preferably forms a coating around the bioactive which is most preferably mixture of starch and Eudragit® S. The "bioactive" is usually the core comprising the drug.

The formulation comprises at least one particle with a core and a coating for the core. The formulation may comprise any suitable coated oral dosage form including capsules; tablets; mini-tablets; pellets; granules; and crystals.

The minimum diameter of each particle is typically at least about $10^{-4}$ m, usually at least about $5 \times 10^{-4}$ m and, preferably, at least about $10^{-3}$ m. The maximum diameter is usually no more than 30 mm, typically no more than 20 mm and, preferably, no more than 10 mm. In preferred embodiments, the particle has a diameter from about 0.2 mm to about 15 mm, preferably from about 1 mm to about 4 mm (e.g. for pellets or mini-tablets) or from about 6 mm to about 12 mm (e.g. for certain tablets or capsules). The term "diameter" refers to the largest linear dimension through the particle.

The formulation may comprise a plurality of particles in order to provide a single dose of the drug(s), particularly in embodiments in which the particle is "small", e.g. having a diameter of less than 5 mm. Multi unit dosage forms comprising particles having a diameter of less than 3 mm are preferred.

The present invention has application in a multi-phasic drug release formulation comprising at least two pluralities of particles, e.g. coated pellets, in the same dosage form, e.g. a capsule, in which the particles of one plurality are differentiated from the particles of the or each other plurality by the coating. The coatings may differ from one plurality to the next in terms of coating thickness or composition, e.g. the ratio and/or identity of components. Multi-phasic drug release formulations would be particularly suitable for suffers of Crohn's disease affecting different regions along the intestine.

The "core" is usually a single solid body. The core may consist of the drug(s) alone or may be a bead of edible material, e.g. sugar, which is coated with a layer comprising the drug(s). More usually, however, the core consists of a mixture of the drug(s) with a filler or diluent material, e.g. lactose or cellulose material such as microcrystalline cellulose; a binder, e.g. polyvinylpyrrolidone ("PVP"); a disintegrant, e.g. Ac-D-Sol™ (i.e. croscarmellose sodium); and/or a lubricant, e.g magnesium stearate. The core may be a compressed granulate comprising at least some of these materials.

Release from formulations according to the present invention is delayed until the intestine and preferably the colon. Release from certain formulations may also be sustained. However, in preferred formulations, release is pulsatile.

A formulation is usually defined as gastric resistant if there is less than 10 wt % drug release in acidic media after 2 hours. Formulations according to the present invention typically display far less than 10 wt % drug release in acidic media and may be considered to be gastric resistant. The formulations usually display less than 1 wt % drug release in acidic media and, typically, display substantially no drug release in acidic media. When starch is combined with an acrylate film forming material to form the coating for the core, typically less than 5% drug release occurs over 5 hours in conditions simulating the stomach and small intestine. On combination of starch with a cellulosic film forming material for the coating for the core, typically less than 10% drug release occurs over 5 hours in conditions simulating the stomach and small intestine.

The time between initial exposure to conditions suitable for drug release and the start of drug release is known as the "lag time". The "lag time" depends on a number of factors including coating thickness and composition. Formulations according to the present invention usually display a lag time in colonic conditions of at least 30 minutes. In most embodiments of the present invention, the lag time is from about 30 minutes to about 3 hours and, in preferred formulations, the lag time is preferably from about 45 minutes to about 2 hours.

The time between initial exposure to conditions suitable for drug release and complete drug release also depends on a number of factors including coating composition and the nature of the drug. In most embodiments of the present invention, this time is usually no more than 5 hours. In preferred embodiments, this time is usually no more than 4 hours.

By way of an example, in embodiments in which a tablet core is coated to a thickness of from 8% to 9% TWG with a coating comprises a high amylose starch and Eudragit S (30:70), the time between initial release and complete release may be less than about 2 hours, preferably less than about 1.5 hours.

In a preferred embodiment, the core is a pellet having diameter of about 1 mm. In another embodiment, the core is a tablet having a diameter of about 8 mm. In both cases, the coating is preferably a 30:70 mixture of high amylose starch, e.g. Eurylon™ 7, and an acrylic polymer, e.g. Eudragit™ S. In both preferred embodiments, the core is coated to a thickness of about 100 μm which is from about 8% to about 9% TWG for the tablet and from about 27% to about 32 wt % for the pellet.

According to a second aspect of the present invention, there is provided a formulation according to the first aspect for use in a method of medical treatment of the human or animal body by therapy.

The core comprises at least one drug. The formulation is usually used to administer a single drug as the sole therapeutically active component. However, more than one drug may be administered in a single formulation.

The formulation of the present invention is designed to administer a wide range of drugs. Suitable drugs include those drugs which are known for intestinal administration using known delayed release oral formulations. The present invention may be used to administer drugs having a local or a systemic effect.

The formulation of the present invention has particular application in the intestinal administration of a drug comprising at least one acidic group such as a carboxylic acid group. Such drugs may be acidic drugs or zwitterionic drugs. An example of such a drug is 5-aminosalicylic acid ("5-ASA").

The identity of the drug(s) in the formulation obviously depends on the condition to be treated. In this connection, the formulation has particular application in the treatment of IBD (including Crohn's disease and ulcerative colitis); IBS; constipation; diarrhoea; infection; and carcinoma, particularly colon or colorectal cancer).

For the treatment or prevention of IBD, the formulation may comprise at least one drug selected from the group consisting of anti-inflammatory agents (e.g. 5-ASA); steroids (e.g. prednisolone; budesonide or fluticasone); immunosuppressants (e.g. azathioprine; cyclosporin; and methotrexate); and antibiotics.

For the treatment or prevention of cancer, the formulation may comprise at least one antineoplastic agent. Suitable antineoplastic agents include fluorouracil; methotrexate; dactinomycin; bleomycin; etoposide; taxol; vincristine; doxorubicin; cisplatin; daunorubicin; VP-16; raltitrexed; oxaliplatin; and pharmacologically acceptable derivatives and salts thereof. For the prevention of colon cancer or colorectal cancer, primarily in patients suffering from colitis, the formulation may comprise the anti-inflammatory agent, 5-ASA.

For the treatment or prevention of IBS, constipation, diarrhoea or infection, the formulation may comprise at least one active agent suitable for the treatment or prevention of these conditions.

Pharmacologically acceptable derivatives and/or salts of the drugs may also be used in the formulation. An example of a suitable salt of prednisolone is methyl prednisolone sodium succinate. A further example is fluticasone propionate.

The present invention has particular application in either the treatment of IBD (particularly, ulcerative colitis) or the prevention of colon cancer or colorectal cancer (primarily in colitis patients), both using 5-ASA. It also has application as a portal of entry of drugs into the systemic circulation via the colon. This is particularly advantageous for peptide and protein drugs which are unstable in the upper gastrointestinal tract. The present invention may also be utilised for the purpose of chronotherapy.

In a third aspect of the invention, there is provided a method of targeting a drug to the colon comprising administering to a patient a formulation as defined above.

In a fourth aspect of the invention, there is provided the use of a formulation as defined above in the manufacture of a medicament for the treatment or prevention of IBD (particularly ulcerative colitis); IBS; constipation; diarrhoea; infection; and cancer.

There is also provided the use of at least one drug selected from anti-inflammatory agents and steroids in the manufacture of a medicament comprising a formulation as defined above for use in the treatment of IBD. In addition, there is also provided the use of at least one antineoplastic agent in the manufacture of a medicament comprising a formulation as defined above for use in the treatment of carcinoma. Further, there is also provided use of 5-ASA in the manufacture of medicament comprising a formulation as defined above for use in the prevention of colon cancer or colorectal cancer.

According to a fifth aspect of the present invention, there is provided a method of medical treatment or prevention of IBD or carcinoma comprises administering to a patient therapeutic amount of a formulation as defined above.

The formulation will typically comprise a therapeutically effective amount of the or each drug which may be from about 0.01 wt % to about 99 wt %, based on the total weight of the formulation. The actual dosage would be determined by the skilled person using his common general knowledge. However, by way of example, "low" dose formulations typically comprise no more than about 20 wt % of the drug, and preferably comprise from about 1 wt % to about 10 wt %, e.g. about 5 wt %, of the drug. "High" dose formulations typically comprise at least 40 wt % of the drug, and preferably from about 45 wt % to about 85 wt %, e.g. about 50 wt % or about 80 wt %.

According to a sixth aspect of the present invention, there is provided a method of preparing a delayed release drug formulation according to the first aspect, said method comprising:

forming a core comprising at least one drug; and
coating the core with a polymer coating preparation comprising a mixture of a first material which is susceptible to attack by colonic bacteria and a second material which has a pH threshold at about pH 5 or above,
wherein the first material comprises a polysaccharide selected from the group consisting of starch; amylose; amylopectin; chitosan; chondroitin sulfate; cyclodextrin; dextran; pullulan; carrageenan; scleroglucan; chitin; curdulan and levan. Preferred polysaccharides are as detailed above. The core is preferably spray coated with said polymer coating preparation.

In embodiments in which the core is formed from a compressed granulate, the method preferably comprises:

dry mixing the drug(s) with at least one excipient to form a dry mixture;
wet granulating at least a portion of said dry mixture to form a wet granulate;
compressing at least a portion of said wet granulate to form said core; and
spray coating said core with said polymer coating preparation to form said delayed release drug formulation. A fluidised bed spray coating machine is preferably used to coat the core(s) with the polymer coating preparation to form the particle(s) of the formulation.

In preferred embodiments, the method comprises:
forming an aqueous dispersion comprising said first material;
forming an alcoholic or aqueous solution comprising said second material; and
adding, preferably drop-wise, at least a portion of said aqueous dispersion of said first material to at least a portion of said alcoholic or aqueous solution of said second material to form said polymer coating preparation.

The first material is usually dispersed in at least one alcohol, preferably a $C_1$ to $C_6$ alcohol, e.g. methanol; ethanol; propan-1-ol; propan-2-ol; butan-1-ol; butan-2-ol; and mixtures thereof, particularly butan-1-ol alone, and then water is usually added subsequently with good agitation. The resulting aqueous dispersion is usually heated to boiling and then cooled with stirring overnight. The purpose of the alcohol(s) is to solvate the first material ready to form the aqueous dispersion. Alternatively, the material can be dispersed directly in water.

The second material is typically dissolved in at least one solvent, for instance water or an organic solvent. The organic solvent may be an alcohol, e.g. methanol; ethanol; propan-2-ol; methyl glycol; butyl glycol; acetone; methyl glycol acetate; and mixtures thereof such as acetone and isopropyl alcohol (e.g. in a ratio of about 4:6). The second material is preferably dissolved in ethanol (preferably from 85 to 98%), under high speed stirring.

The polymer coating preparation is preferably formed by adding an appropriate quantity of the aqueous dispersion to the alcoholic solution, drop-wise under fast stirring. The further excipient(s) such as a plasticiser (e.g. triethyl citrate) and/or a lubricant (e.g. glyceryl monostearate) is usually added to the preparation while stirring.

A number of preferred embodiments of the present invention will now be described with reference to the drawings, in which:—

EXAMPLE 1

Preparation of Prednisolone Tablets

Figure 1:
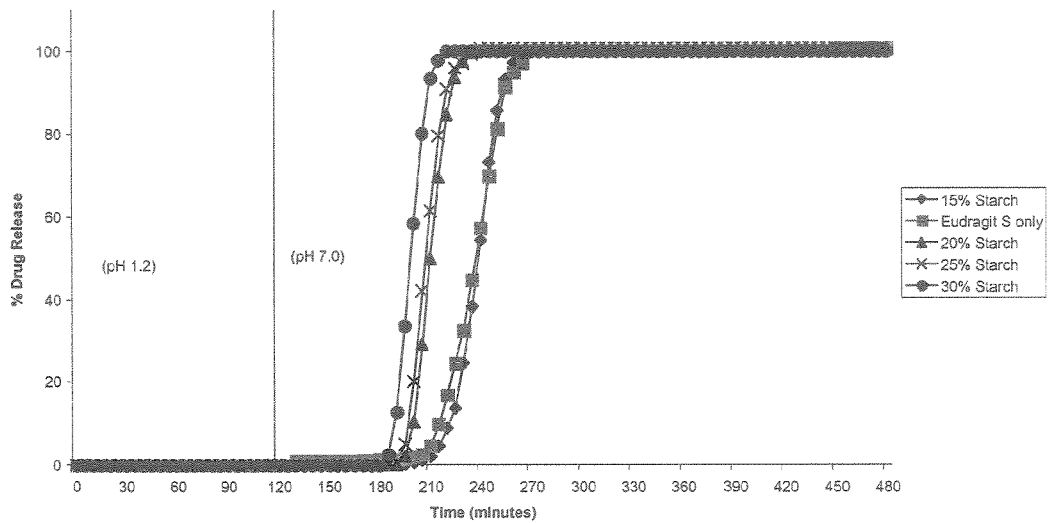
FIG. 1 is a graph depicting the dissolution profiles of mixed film coated prednisolone tablets at 5% TWG and Eudragit® S coated tablets at 5% TWG in pH 7.0 buffer.
Figure 2:
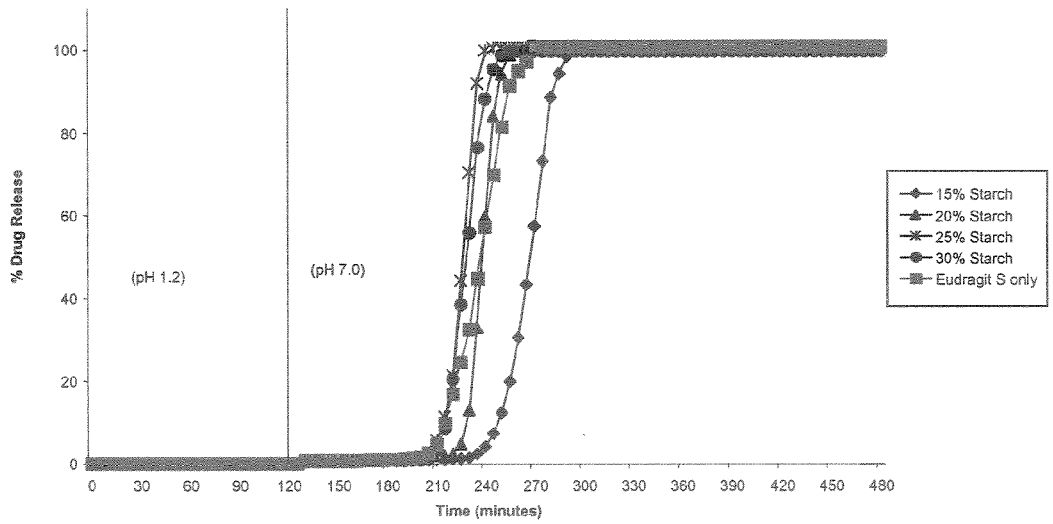
FIG. 2 is a graph depicting the dissolution profiles mixed film coated tablets as for FIG. 1 but with 6% TWG.
Figure 3:
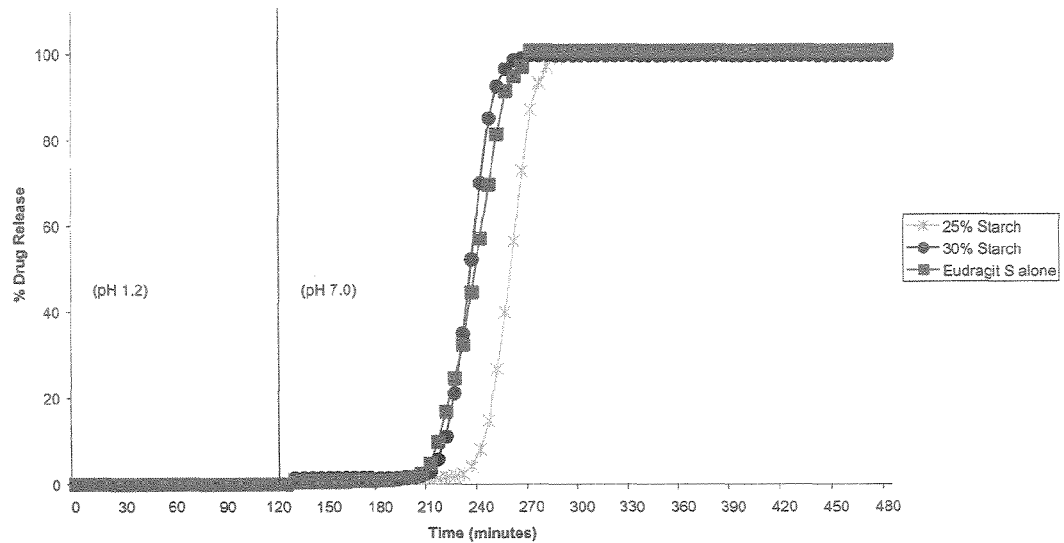
FIG. 3 is a graph depicting the dissolution profiles of mixed film coated tablets as for FIG. 1 but with 7.4% TWG.
Figure 4:
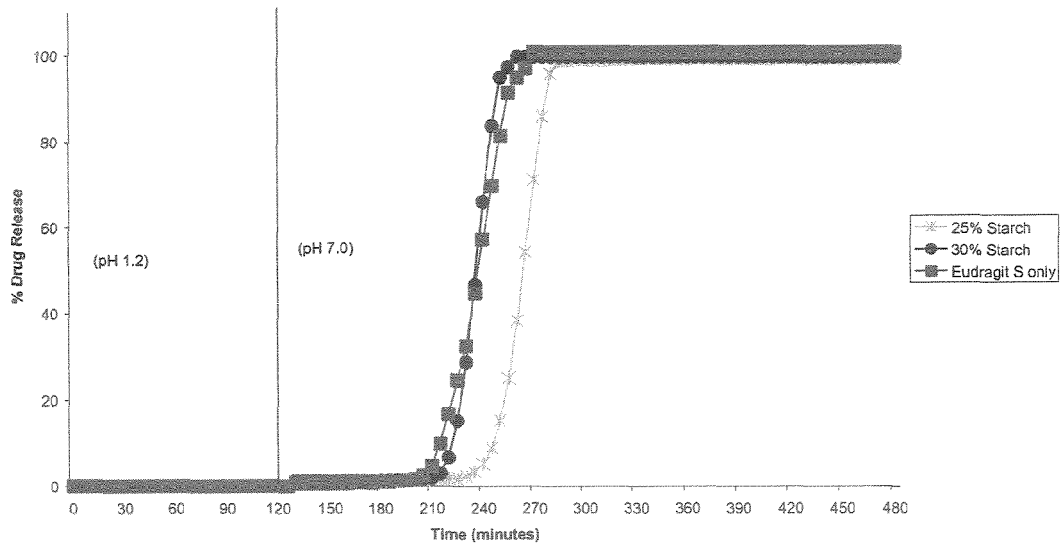
FIG. 4 is a graph depicting the dissolution profiles mixed film coated tablets as for FIG. 1 but with 8.3% TWG.
Figure 5:
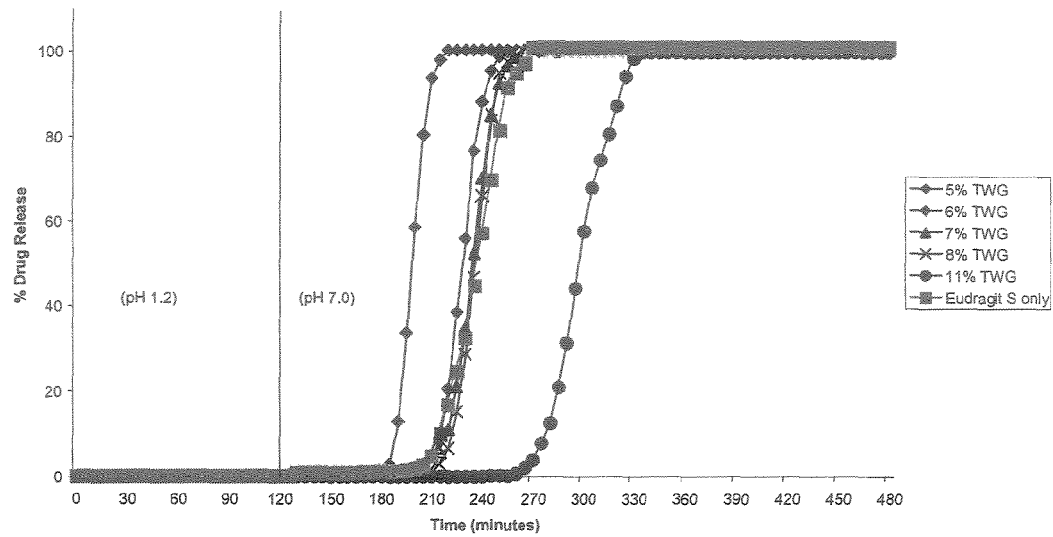
FIG. 5 is a graph depicting the dissolution profiles of prednisolone tablets coated with 30% starch:70% Eudragit S at various polymer weight gains and Eudragit® S coated tablets at 5% TWG.

Prednisolone tablets (weight 200 mg, diameter 8 mm and standard bi-concave) were prepared according to the following formula:

| | |
|---|---|
| Lactose | 85% |
| Prednisolone | 5% |
| PVP | 5% |
| Ac-di-sol | 4% |
| | (⅔ intragranular and ⅓ extragranunular) |
| Magnesium stearate | 1% |
| | (extragranular) |

Prednisolone was dry mixed with the excipients and then wet granulated. Granules of 500-710 μm size fraction were compressed using a single punch tabletting machine (Manesty, UK).

Formulation for Starch Aqueous Dispersion

| | |
|---|---|
| Eurylon 7 | 16 g |
| Butan-1-ol | 32 g |
| Water | 352 g |

Eurylon™ 7 starch was dispersed well in the butan-1-ol and water subsequently added with good agitation. The resulting dispersion was then heated to boiling, and cooled with stirring overnight. The % solids content of the cooled dispersion was calculated based on the final weight of the dispersion (allowing for evaporation during heating).

Formulation for Eudragit® S solution

Eudragit® S solution was prepared by dissolution of Eudragit® S 100 polymer in 96% ethanol under high speed stirring. The final solution contained approximately 6% polymer solids.

Mixed Starch-Eudragit® Coating Dispersion

Appropriate quantities of the starch dispersion and Eudragit® solution were mixed to give the required ratios stated as the dry polymer substance. The starch was always added to the Eudragit® solution drop-wise under fast stirring. The resulting dispersions were left ring for two hours before the addition of the excipients and for another two hours after adding excipients. The added excipients were:

| | |
|---|---|
| Triethyl citrate | 10% of dry polymer substance |
| Glyceryl Monostearate | 5% of dry polymer substance |

The final mixed polymer coating preparation was film coated onto the tablets using a fluidised bed spray coating machine. Coating thickness was estimated as % weight increase of the tablets following coating (% TWG)

The spray coating parameters were as follows:

| Flow rate | 0.7 ml/minute |
|---|---|
| Atomising pressure | 0.2 bar |
| Coating temperature | 40° C. |

In Vitro Tests

Starch dispersion was prepared from Eurylon 7, a "high amylose" starch, and mixed with a solution of Eudragit® S in ethanol. The composition and preparation method for the coating dispersions are as described above. Various starch/Eudragit® S combinations were prepared containing 15%, 20%, 25%, 30% and 35% starch. The mixed Eudragit®/starch coating dispersions were then film coated onto prednisolone tablets prepared according to the method described above. Tablets were coated to varying thicknesses, calculated as total weight gain on the polymer, to also determine the optimum coating thickness. The coating mixture yielded good quality films up to a ratio of 30% starch.

Coated tablets were then tested in vitro for drug release in varying pH buffer solution. The optimum starch/Eudragit® S ratio and coating weight gain was primarily based on comparison of the dissolution profile with conventional Eudragit® S coated tablets.

Results are shown in FIGS. 1-7.

Very surprisingly, these mixed film coated tablets were able to resist drug release in pH 1.2 HCl simulating the gastric media (see the left-hand side of the graphs of FIGS. 1-6).

Figure 6:
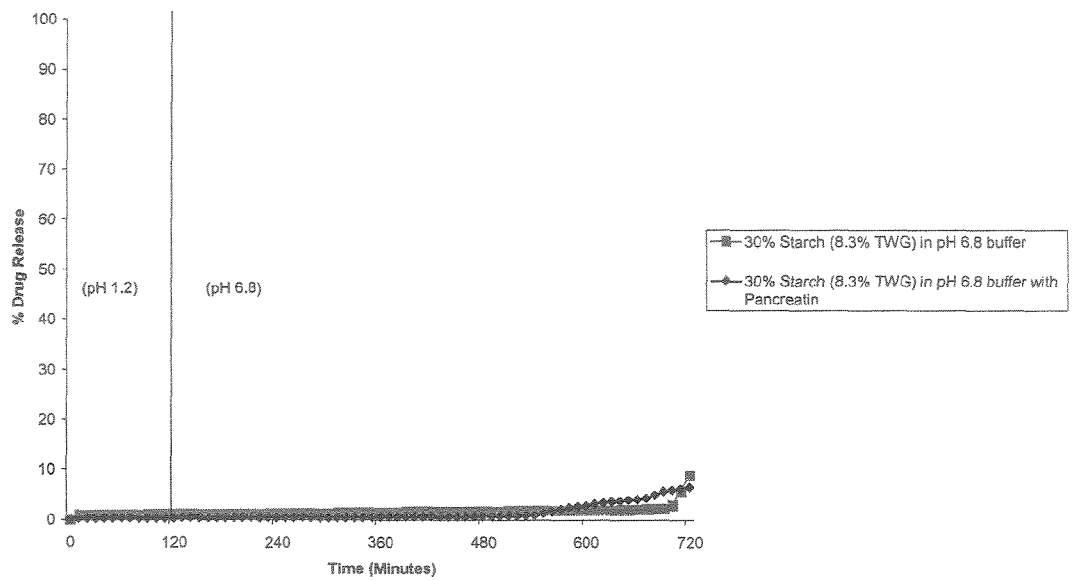
FIG. 6 is a graph depicting the dissolution profile of prednisolone tablets coated with 30% starch:70% Eudragit® S in pH 6.8 buffer, with and without pancreatin.

There was also no drug release from any of the coated tablets for up to 12 hours in pH 6.8 simulating the small intestinal media (see FIG. 6). Previous in vitro studies using mixed amylose/acrylate polymers based on the water-insoluble Eudragit® RL and RS products showed uncontrollable swelling and rapid drug release in acid and buffer (Milojevic et al., 1996).

Drug release profiles from the coated tablets in pH 7.0 buffer media are shown in FIGS. 1 to 5. Based on an analysis of the dissolution profiles, tablets coated with a 30% starch/Eudragit® mixture to a film thickness equivalent to a TWG of 8.3% was judged to be optimal, and were further tested to assess the digestibility of the starch component of the film.

Figure 7:
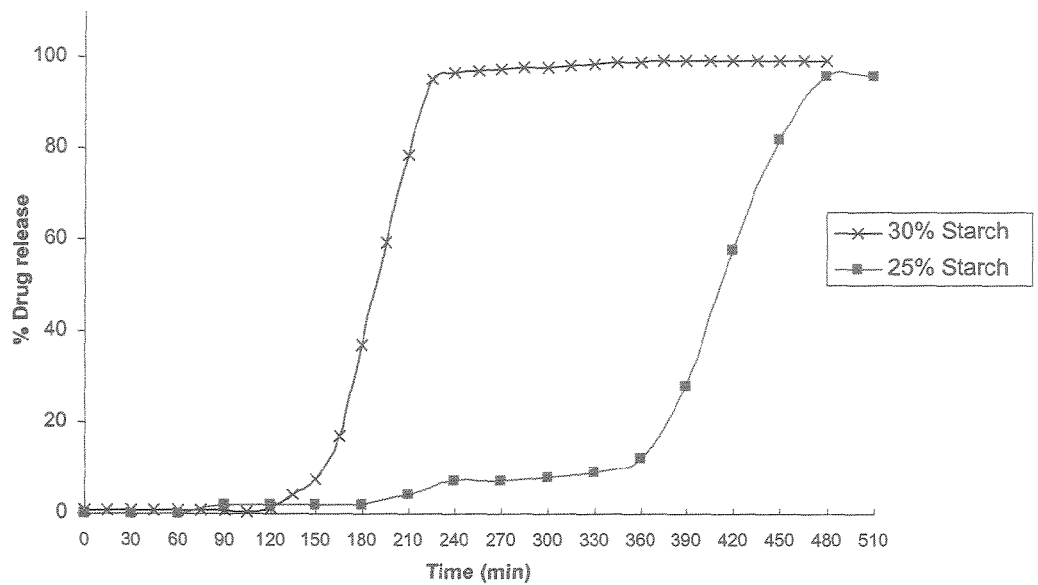
FIG. 7 is a graph depicting drug release from prednisolone tablets coated to 8.3% TWG in pH 6.8 buffer containing 50 U/ml amylase.

The tablets were dissolution tested in pH 6.8 buffer containing 50 U (units)/ml α-amylase derived from *B. licheniformis* (see FIG. 7). A dissolution test was also carried out in pH 6.8 media with pancreatin to test whether the starch is digestible by pancreatic α-amylase (see FIG. 6).

Results of the dissolution tests in the presence of the enzymes show that the starch component of the film is indigestible in the presence of the pancreatin (suggesting resistance in the small intestine), but drug release occurred within three hours in the presence of α-amylase from *B. licheniformis*. These results provide evidence that the mixed film resists drug release in simulated conditions of the upper gastrointestinal tract but is digestible in the presence of bacterial enzymes (even at a pH lower than the threshold pH of the Eudragit® S polymer for dissolution)

In Vivo Study in Healthy Volunteers

Following the surprising success of the in vitro studies with the mixed starch/Eudragit® S film coated tablets; the performance of the dosage form was tested in healthy human subjects. The tablets were radio-labelled with indium-ill and administered to eight healthy male volunteers on three separate occasions. The transit and disintegration site of the tablet in the gastrointestinal tract was followed using a gamma camera.

The time and site of disintegration of these mixed film tablets can be seen in Table 1. The results show surprisingly excellent colonic targeting, with tablet disintegration occurring primarily in the colon.

The results from the healthy volunteer study provides evidence that starch and Eudragit® mixed at a proportion of 30% starch to 70% Eudragit® S and coated onto tablets a approximately 8.3% TWG, is able to resist tablet disintegration in the stomach and small intestine but trigger disintegration in the colon.

Table 1 shows the site and time of disintegration of 30% starch and 70% Eudragit® S coated tablets in eight healthy male volunteers on three separate occasions.

Key to Table 1:
"Fasted"—tablet given on an empty stomach;
"Pre-fed"—tablet given on an empty stomach, but meal administration 30 minutes post dose; and
"Fed"—tablet given after breakfast.
"ICJ"—ileocolonic junction;
"AC"—ascending colon;
"HF"—hepatic flexure; and
"SF"—splenic flexure.

TABLE 1

| Subject | Treatment 1 (Fasted) | | Treatment 2 (Partial fasted) | | Treatment 3 (Fed) | |
|---|---|---|---|---|---|---|
| | Site | Time | Site | Time | Site | Time |
| 1 | ICJ | 237 | ICJ | 244 | AC | 240 |
| 2 | AC | 200 | ICJ | 339 | AC | 316 |
| 3 | AC | 201 | ICJ | 350 | AC | 510 |
| 4 | AC | 292 | HF | 390 | AC | 415 |
| 5 | TC | 465 | SF | 678 | AC | 555 |
| 6 | Subject did not attend study day | — | AC | 523 | AC | 523 |
| 7 | AC | 274 | AC | 244 | SF | 465 |
| 8 | AC | 614 | Tablet did not empty from stomach | — | AC | 455 |

EXAMPLE 2

Tablets (weight 200 mg; diameter 8 mm; standard bi-concave) containing 5 wt % 5-aminosalicylic acid in place of wt % prednisolone were prepared and coated with a polymer mixture comprising 70% Eudragit® S:30% starch (Eurylon™ 7) to 5%, 6%, 7% and 8.3% TWG in accordance with the procedure given in Example 1.

Figure 8:
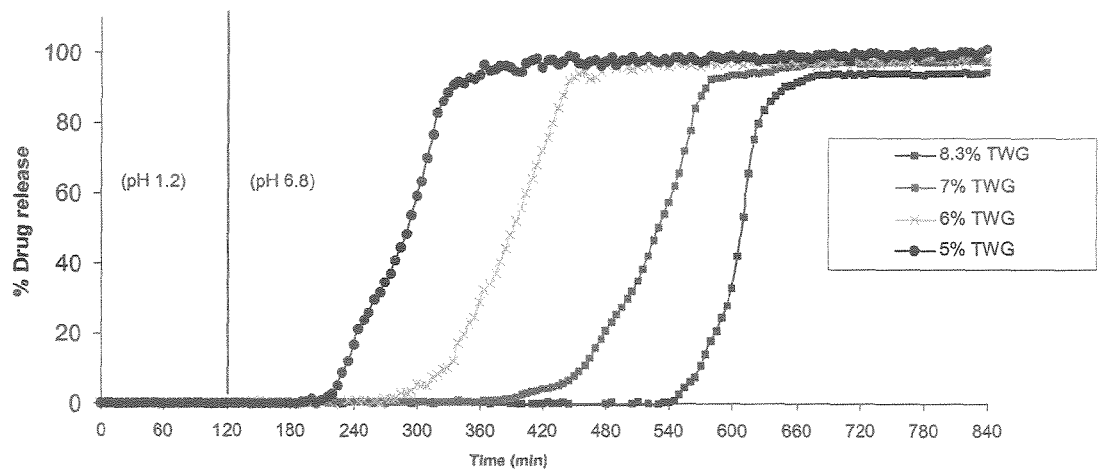
FIG. 8 is a graph depicting the dissolution profile of 5-ASA tablets coated with 30% starch:70% Eudragit® S to 8.3% TWG in pH 6.8 buffer.

The 5-ASA tablets with different weight gains of 5, 6, 7 and 8.3% were then tested in vitro for drug release in pH 6.8 buffer in the absence of α-amylase. FIG. 8 indicates that for the 5-ASA tablet coated to 8.3% TWG there was no release of 5-ASA for about 9 hours with almost complete release after about 11 hours.

Figure 9:
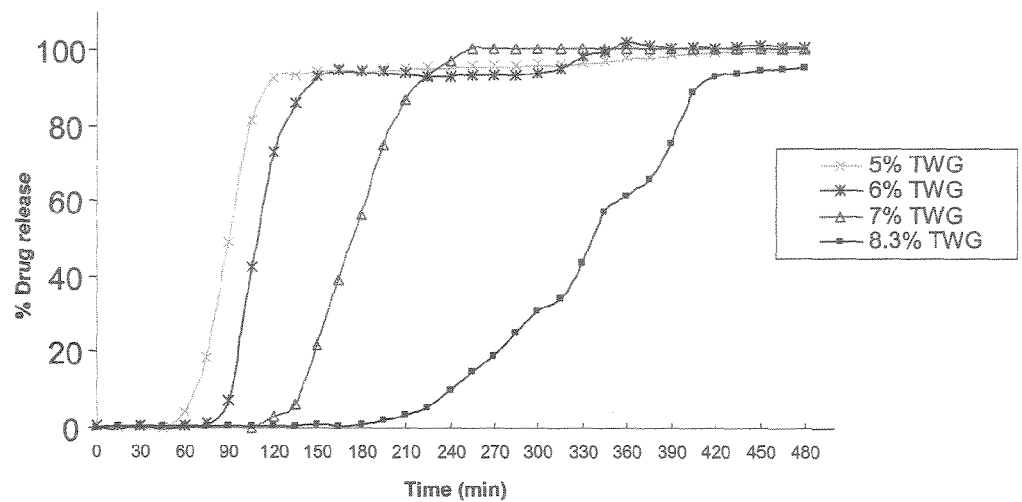
FIG. 9 is a graph depicting the dissolution profiles of 5-ASA tablets coated with 30% starch:70% Eudragit® S to various polymer weight gains in pH 6.8 buffer containing 50 U/ml amylase.

The 5-ASA tablets with each of the different TWGs were then tested in vitro for drug release in the presence of 50 U/ml α-amylase. FIG. 9 indicates that drug release was much faster for all TWGs in the presence of α-amylase.

The 5-ASA tablet coated to 7% TWG gave a similar lag-time in pH 6.8 buffer (about 2 hours) as a 5 wt % prednisolone tablet coated to 8.3% TWG. Without wishing to be bound by any particular theory, this result may be explained by 5-ASA exhibiting acidic properties as it dissolves in the near neutral buffer, thus reducing the pH at the tablet core/polymer boundary layer relative to the bulk medium and consequently retarding dissolution of the polymer coating.

EXAMPLE 3

Tablets (weight 200 mg; diameter 8 mm; standard bi-concave) containing 5 wt % prednisolone were prepared and coated with a polymer mixture comprising 70% Eudragit® S:30% starch to 8.3% TWG in accordance with the procedure given in Example 1. The starch used was either a "high" amylose maize starch (Eurylon™ 7; ~70 wt % amylose) or a "low" amylose starch (natural maize starch; ~27 wt % amylose; Sigma, Poole, UK).

The tablets were then tested in vitro for drug release in pH 7 buffer without amylase and then in pH 6.8 buffer, with and without 50 U/ml α-amylase.

Figure 10:
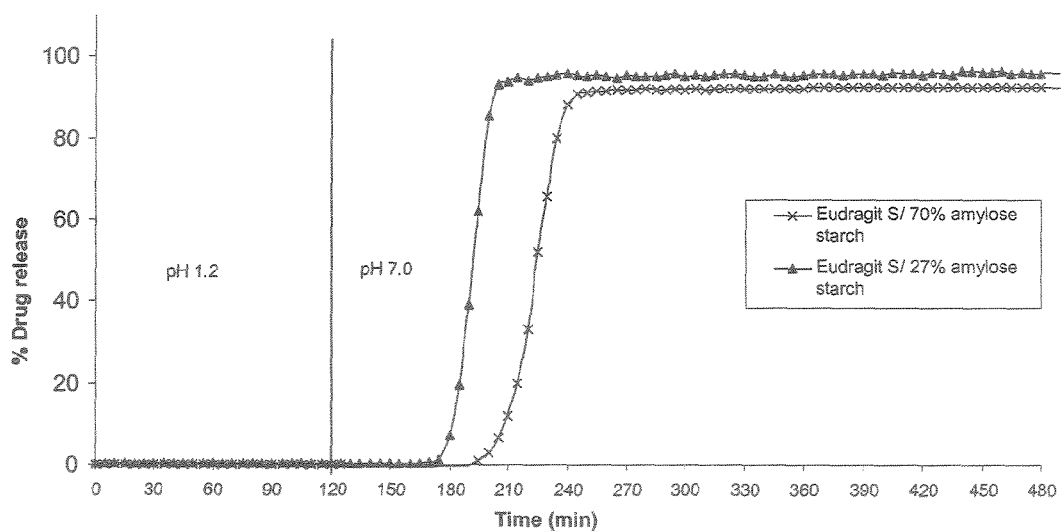
FIG. 10 is a graph depicting the dissolution profiles of prednisolone tablets coated with 70% Eudragit® S:30 starch having either 70 wt % or 27 wt % amylose in pH 7 buffer.
Figure 11:
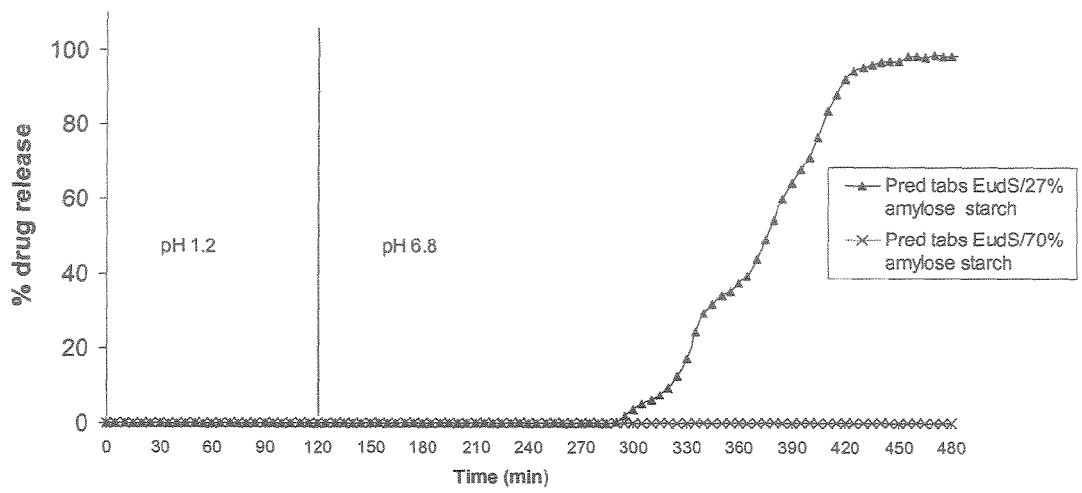
FIG. 11 is a graph depicting the dissolution profiles of prednisolone tablets as for FIG. 10 in pH 6.8 buffer.
Figure 12:
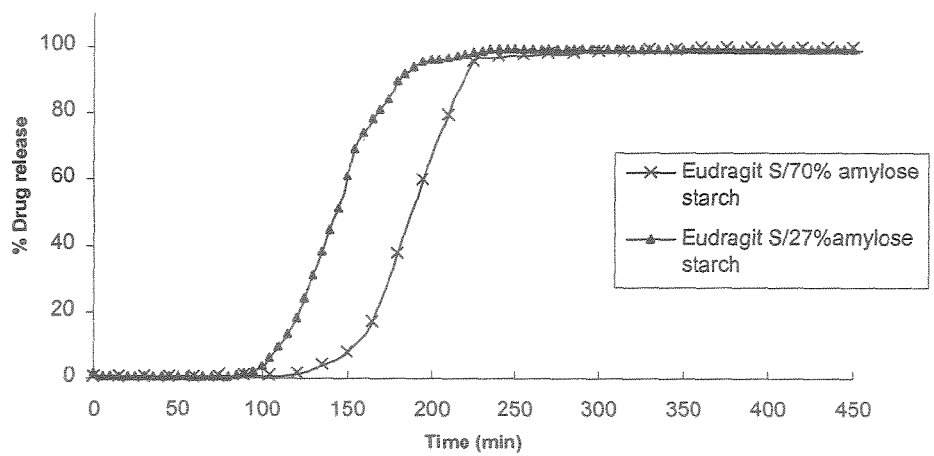
FIG. 12 is a graph depicting the dissolution profiles of the prednisolone tablets as for FIG. 10 in pH 6.8 buffer containing 50 U/ml amylase.

FIGS. 10 and 11 indicate that drug release is quicker using "low" amylose starch. FIG. 11 indicates that there is a lag-time of about 2.5 hours in small intestinal conditions for the "low" amylose starch tablets which was shorter than the lag time for the "high" amylose starch tablets. This result may be explained by noting that amylopectin is more water soluble than amylose. Thus, the greater the proportion of amylopectin, the quicker the coating dissolves in aqueous solution. FIG. 12 indicates that drug release is substantially quicker in the presence of α-amylase.

The tablets having the coating containing "low" amylose starch have also been demonstrated (using the same procedure as for FIG. 6) to be indigestible to pancreatin for several hours, further substantiating the resistance of the "low" amylose system in the small intestine. Such resistance is surprising as amylopectin is a substrate of pancreatic amylase (present in pancreatin) and, therefore, digestion of the coating and drug release would have been expected.

EXAMPLE 4

Tablets (weight 200 mg; diameter 8 mm; standard bi-concave) containing 5 wt % prednisolone were prepared and coated with a polymer mixture comprising 70% Eudragit® L:30% starch (Eurylon™ 7) to 8.3% TWG in accordance with the procedure given in Example 1.

The tablets were then tested in vitro for drug release in pH 5.5 buffer, first without amylase and then with 50 U/ml α-amylase.

Figure 13:
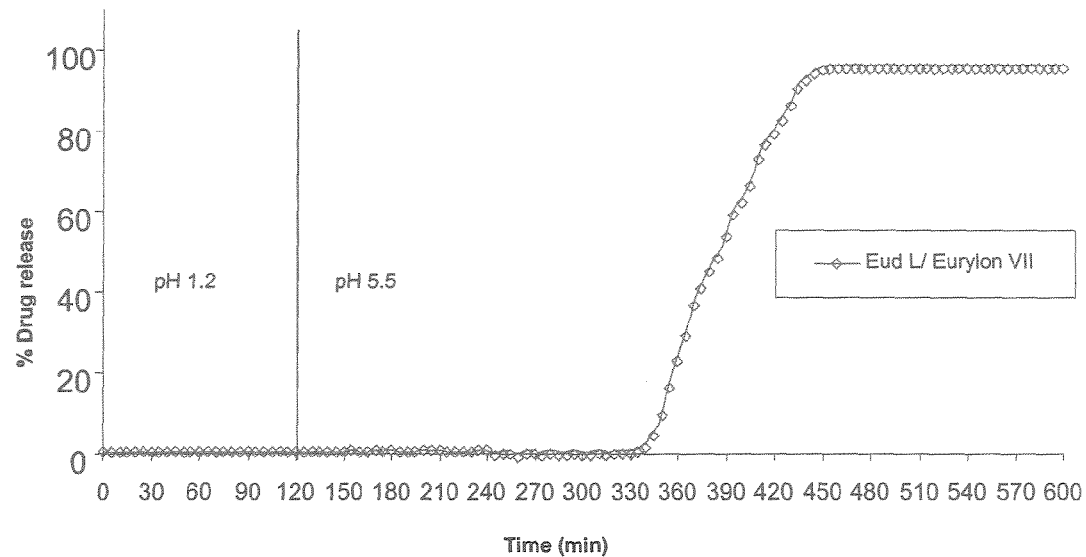
FIG. 13 is a graph depicting the dissolution profile of prednisolone tablets coated with 70% Eudragit® L:30% starch to 8.3% TWG in pH 5.5 buffer.
Figure 14:
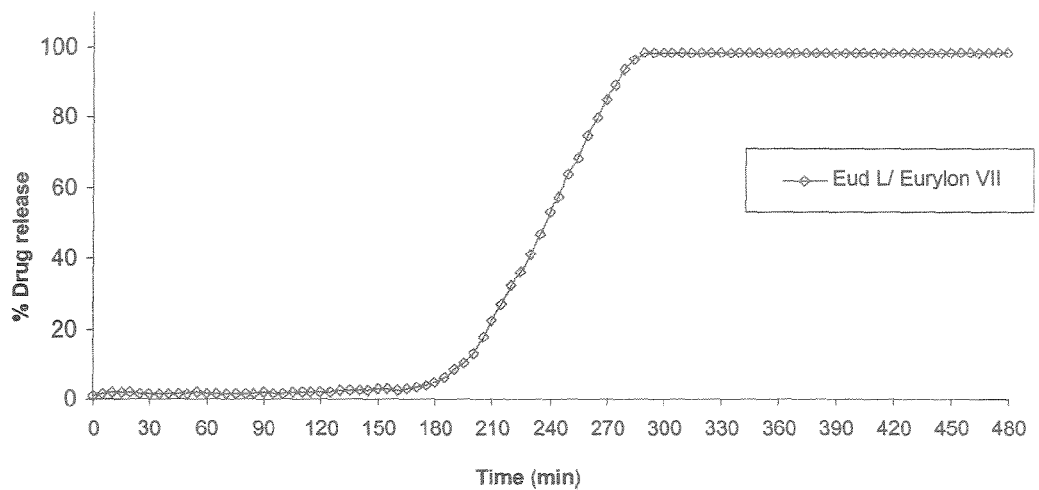
FIG. 14 is a graph depicting the dissolution profile of prednisolone tablets as for FIG. 13 in pH 5.5 buffer containing 50 U/ml amylase.

FIG. 13 indicates a lag time of just under 4 hours in small intestinal conditions. However, in the presence of α-amylase, the lag-time was about 3 hours (FIG. 14). The results indicate that this coating system could be used for drug release in the proximal small intestine.

EXAMPLE 5

Tablets (weight 200 mg; diameter 8 mm; standard bi-concave) containing 5 wt % prednisolone were prepared and coated with a polymer mixture comprising 70% hydroxypropyl methylcellulose acetate succinate ("HPMCAS"):30% starch (Eurylon' 7) to 8.3% TWG generally in accordance with the procedure given in Example 1. The HPMCAS (ShinEtsu, Japan) used had the granular grade HG with a pH threshold of 6.8. The HPMCAS-HG was dissolved in 90% ethanol and the aqueous dispersion of starch added to it.

The tablets were then tested in vitro for drug release in pH 6.5 buffer, first without amylase and then with 50 U/ml α-amylase. Further tablets were then tested in vitro for drug release in pH 6.8 buffer in the absence of α-amylase.

Figure 15:
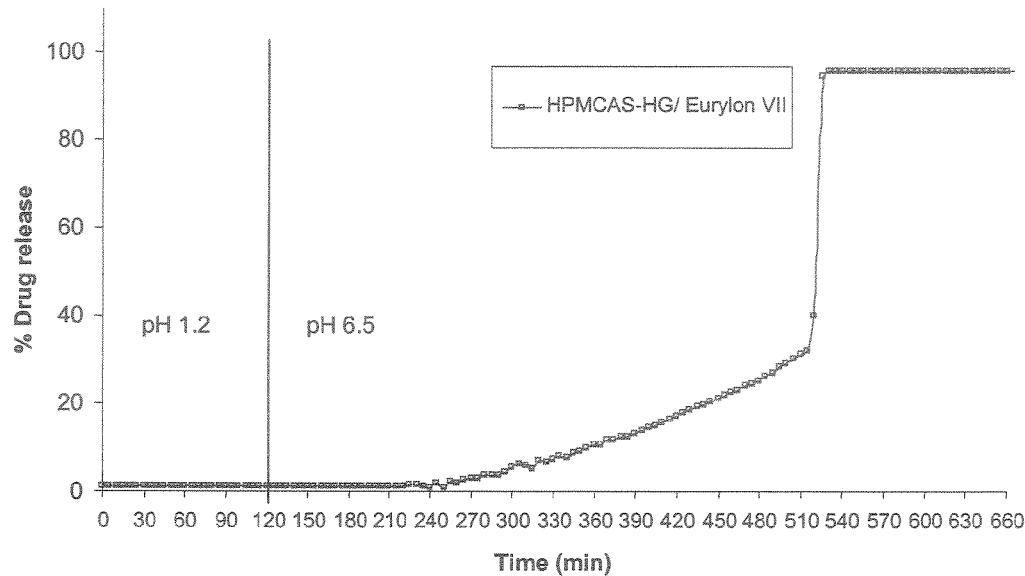
FIG. 15 is a graph depicting the dissolution profile of prednisolone tablets coated with 70% HPMCAS-HG:30% starch in pH 6.5 buffer.

FIG. 15 indicates that the coating had a tendency to swell below the pH threshold of the HMPCAS-HG, allowing slow diffusion of the drug out of the formulation prior to dissolution of the coating and a burst of drug release. The lag-time prior to the onset of diffusion in pH 6.5 buffer in the absence of α-amylase was about 2 hours which would be sufficient to retard release until the distal small intestine. Diffusion continued for approximately an additional 4.5 hours resulting in almost 40% of the drug diffusing out prior to the burst release.

Figure 16:
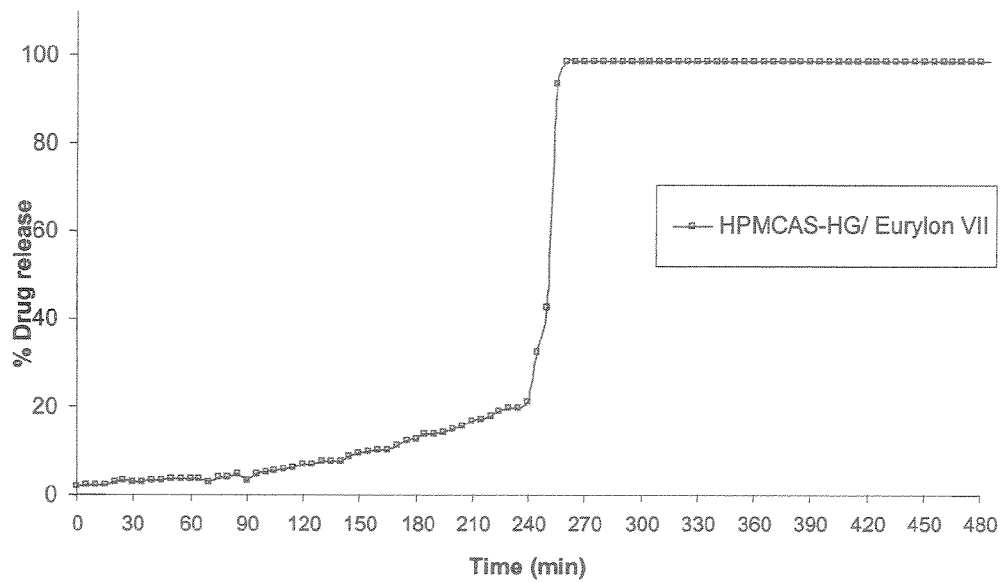
FIG. 16 is a graph depicting the dissolution profile of the prednisolone tablets as for FIG. 15 in pH 6.5 buffer containing 50 U/ml amylase.
Figure 17:
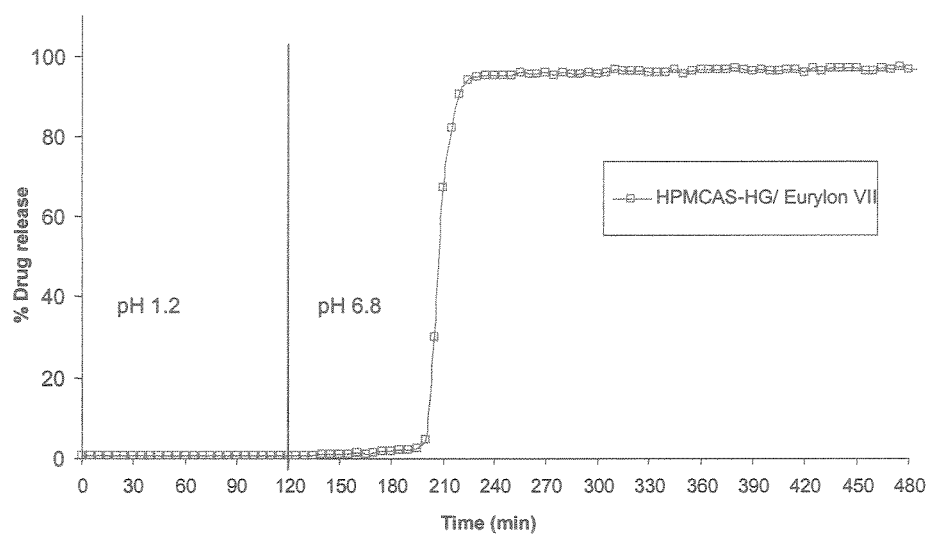
FIG. 17 is a graph depicting the dissolution profile of the prednisolone tablets as for FIG. 15 in pH 6.8 buffer.

In the presence of α-amylase, there was no lag time in pH 6.5 buffer with diffusion starting immediately and releasing 20% of the drug prior to the onset of the burst release (FIG. 16). However, at pH 6.8, this diffusion phenomenon does not exist, presumably due to the faster dissolution of the system (FIG. 17).

It will be appreciated that the invention is not restricted to the details described above with reference to the preferred embodiments but that numerous modifications and variations can be made without departing from the spirit or scope of the invention as defined by the following claims.

The invention claimed is:

1. A delayed release drug formulation suitable for delivering a drug to the colon of a subject, the formulation comprising a particle with a core and a coating for the core, the core comprising a drug and the coating comprising a homogenous mixture of a first material which is susceptible to attack by colonic bacteria and a second material which is a film-forming acrylate polymer having a pH threshold at about pH 5 or above which is the pH below which the second material is insoluble and at or above which the second material is soluble and dissolution of the second material is triggered by surrounding medium in the colon, wherein the first material is selected from the group consisting of amylopectin; and starch having no more than 75 wt % amylose;
wherein a ratio of the first material to the second material in the mixture is from 15:85 to less than 99:1,
wherein the coating has a thickness as measured by theoretical weight gain of from about 4% to about 35%, and
wherein release of the drug is delayed until the colon of the subject.

2. A formulation as claimed in claim 1, wherein the first material is starch having no more than 75 wt % amylose.

3. A formulation as claimed in claim 1, wherein the second material is an anionic copolymer of (meth)acrylic acid and (meth)acrylic acid $C_{1-4}$ alkyl ester.

4. A formulation as claimed in claim 3, wherein the second material is an anionic co-polymer of methacrylic acid and methacrylic acid methyl ester.

5. A formulation as claimed in claim 4, wherein the ratio of methacrylic acid to methacrylic acid methyl ester is about 1:2.

6. A formulation as claimed in claim 1, wherein the second material is an anionic poly(methacrylic acid/methyl methacrylate) copolymer with an acid to ester ratio of 1 to 2, a molecular weight of approximately 135,000 and a pH threshold of approximately 7.

7. A formulation as claimed in claim 3, wherein the second material is a copolymer of methacrylic acid and ethyl acrylate.

8. A formulation as claimed in claim 1, wherein the proportion of the first material to the second material is up to about 35:65.

9. A formulation as claimed in claim 8, wherein the proportion of the first material to the second material is from 15:85 to 35:65.

10. A formulation as claimed in claim 1, wherein the minimum diameter of the particle is at least $5 \times 10^{-4}$ m.

11. A formulation as claimed in claim 1, wherein the thickness of the coating as measured by theoretical weight gain of the coated formulation is from 5 to 10%.

12. A formulation as claimed in claim 1, wherein the thickness of the coating as measured by theoretical weight gain of the coated formulation is from 15 to 35%.

13. A formulation as claimed in claim 1, wherein the coating has a thickness of from about 10 μm to about 150 μm.

14. A formulation as claimed in claim 1, wherein the drug comprises at least one acidic group.

15. A formulation as claimed in claim 1, wherein the drug is an anti-inflammatory agent.

16. A formulation as claimed in claim 14, wherein the drug is 5-aminosalicylic acid.

17. A formulation as claimed in claim 1, wherein the drug is a steroid.

18. A formulation as claimed in claim 17, wherein the drug is selected from the group consisting of prednisolone; budesonide; fluticasone and pharmaceutically acceptable salts thereof.

19. A formulation as claimed in claim 1, wherein the drug is an antineoplastic agent.

20. A method of delivering a drug to the colon of a subject, the method comprising
providing a delayed release drug formulation suitable for delivering a drug to the colon of a subject, the formulation comprising a particle with a core and a coating for the core, the core comprising a drug and the coating comprising a homogenous mixture of a first material which is susceptible to attack by colonic bacteria and a second material which is a film-forming acrylate polymer having a pH threshold at about pH 5 or above which is the pH below which the second material is insoluble and at or above which the second material is soluble and dissolution of the second material is triggered by surrounding medium in the colon, wherein the first material is selected from the group consisting of amylopectin; and starch having no more than 75 wt % amylose,
wherein a ratio of the first material to the second material in the mixture is from 15:85 to less than 99:1,
wherein the coating has a thickness as measured by theoretical weight gain of from about 4% to about 35%, and
wherein release of the drug is delayed until the colon of the subject.

21. A formulation as claimed in claim 1, wherein the first material is starch having no more than 50 wt % amylose and at least 50 wt % amylopectin.

22. A formulation as claimed in claim 1, wherein the first material is amylopectin.

23. A delayed release drug formulation suitable for delivering a drug to the colon of a subject, the formulation comprising a particle with a core and a coating for the core, the core comprising a drug and the coating comprising a homogenous mixture of a first material which is susceptible to attack by colonic bacteria and a second material which is a film-forming acrylate polymer having a pH threshold at about pH 5 or above which is the pH below which the second material is insoluble and at or above which the second material is soluble and dissolution of the second material is triggered by surrounding medium in the colon, wherein the first material is starch which requires no processing prior to use,
wherein a ratio of the first material to the second material in the mixture is from 15:85 to less than 99:1,
wherein the coating has a thickness as measured by theoretical weight gain of from about 4% to about 35%, and
wherein release of the drug is delayed until the colon of the subject.

24. A delayed release drug formulation suitable for delivering a drug to the colon of a subject, the formulation comprising a particle with a core and a coating for the core, the core comprising a drug and the coating comprising a homogenous mixture of a first material which is susceptible to attack by colonic bacteria and a second material which is a film-forming acrylate polymer having a pH threshold at about pH 5 or above which is the pH below which the second material is insoluble and at or above which the second material is soluble and dissolution of the second material is triggered by surrounding medium in the colon, wherein the first material comprises at least one polysaccharide selected from the group consisting of starch; amylose; amylopectin; chitosan; chondroitin sulphate; cyclodextrin; dextran; pullulan; carrageenan; scleroglucan; chitin; curdlan; and levan, wherein the first material and the second material are present in a proportion of about 30:70, wherein the coating has a thickness as measured by theoretical weight gain of from about 4% to about 35%, and wherein release of the drug is delayed until the colon of the subject.

25. A delayed release drug formulation suitable for delivering a drug to the colon of a subject, the formulation comprising a particle with a core and a coating for the core, the core comprising a drug and the coating comprising a homogenous mixture of a first material which is susceptible to attack by colonic bacteria and a second material which is a film-forming acrylate polymer having a pH threshold at about pH 5 or above which is the pH below which the second material is insoluble and at or above which the second material is soluble and dissolution of the second material is triggered by surrounding medium in the colon, wherein the first material comprises at least one polysaccharide selected from the group consisting of starch; amylose; amylopectin; chitosan; chondroitin sulphate; cyclodextrin; dextran; pullulan; carrageenan; scleroglucan; chitin; curdlan; and levan, wherein release of the drug is delayed until the colon of the subject,
wherein a ratio of the first material to the second material in the mixture is from 15:85 to less than 99:1,
wherein the coating has a thickness as measured by theoretical weight gain of from about 4% to about 35%, and
and wherein said formulation displays a lag time in colonic conditions of at least 30 minutes.

26. A delayed release drug formulation suitable for delivering a drug to the colon of a subject, the formulation comprising a particle with a core and a coating for the core, the core comprising a drug and the coating comprising a homogenous mixture of a first material which is susceptible to attack by colonic bacteria and a second material which is a film-forming acrylate polymer having a pH threshold at about pH 5 or above which is the pH below which the second material is insoluble and at or above which the second material is soluble and dissolution of the second material is triggered by surrounding medium in the colon, wherein the first material is selected from the group consisting of cyclodextrin; and dextran,
wherein a ratio of the first material to the second material in the mixture is from 15:85 to less than 99:1,
wherein the coating has a thickness as measured by theoretical weight gain of from about 4% to about 35%, and
wherein release of the drug is delayed until the colon of the subject.

27. A formulation as claimed in claim 21, wherein the polysaccharide is starch comprising up to 100% amylopectin.

28. A delayed release drug formulation suitable for delivering a drug to the colon of a subject, the formulation comprising a particle with a core and a coating for the core, the core comprising a drug and the coating comprising a homogenous mixture of starch which is susceptible to attack by colonic bacteria and a second material which is a film-forming acrylate polymer having a pH threshold at about pH 5 or above which is the pH below which the second material is insoluble and at or above which the second material is soluble and dissolution of the second material is triggered by surrounding medium in the colon,
   wherein a ratio of the first material to the second material in the mixture is from 15:85 to less than 99:1,
   wherein the coating has a thickness as measured by theoretical weight gain of from about 4% to about 35%, and
   wherein release of the drug is delayed until the colon of the subject.

* * * * *